(12) United States Patent
Phillips et al.

(10) Patent No.: US 10,335,169 B2
(45) Date of Patent: Jul. 2, 2019

(54) ANGLED ORTHOPAEDIC DRIVER

(71) Applicant: Symmetry Medical Manufacturing, Inc., Warsaw, IN (US)

(72) Inventors: Alton Phillips, Warsaw, IN (US); John Conley, Silver Lake, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 694 days.

(21) Appl. No.: 14/853,413

(22) Filed: Sep. 14, 2015

(65) Prior Publication Data
US 2017/0071609 A1 Mar. 16, 2017

(51) Int. Cl.
*A61B 17/16* (2006.01)

(52) U.S. Cl.
CPC ................. *A61B 17/1631* (2013.01)

(58) Field of Classification Search
CPC ................ A61B 17/1631; A61B 17/1633
See application file for complete search history.

(56) References Cited

U.S. PATENT DOCUMENTS

| | | | |
|---|---|---|---|
| 5,030,219 A | 7/1991 | Matsen, III et al. | |
| 5,863,159 A | 1/1999 | Lasko | |
| 6,120,507 A | 9/2000 | Allard et al. | |
| 6,673,115 B2 | 1/2004 | Resch et al. | |
| 6,875,237 B2 | 4/2005 | Dye | |
| 7,316,690 B2 | 1/2008 | Parker et al. | |
| 7,785,329 B2 * | 8/2010 | Lechot | A61B 17/1631 606/81 |
| 7,942,879 B2 | 5/2011 | Christie et al. | |
| 8,038,719 B2 | 10/2011 | Gunther | |
| 8,348,959 B2 | 1/2013 | Wolford et al. | |
| 8,439,947 B2 | 5/2013 | Howard et al. | |
| 8,444,646 B2 | 5/2013 | Long et al. | |
| 8,465,491 B2 | 6/2013 | Yedlicka et al. | |
| 8,480,674 B1 | 7/2013 | Roger et al. | |
| 8,518,044 B2 | 8/2013 | Sidebotham et al. | |
| 8,640,575 B2 | 2/2014 | Huang | |
| 8,778,028 B2 | 7/2014 | Gunther et al. | |
| 8,801,716 B2 | 8/2014 | Merdiew | |
| 9,814,470 B2 * | 11/2017 | Weekes | A61B 17/1666 |
| 2005/0038443 A1 | 2/2005 | Hedley et al. | |
| 2011/0152867 A1 * | 6/2011 | Petrzelka | A61B 17/1631 606/80 |
| 2012/0239042 A1 | 9/2012 | Lappin et al. | |
| 2013/0211408 A1 * | 8/2013 | Kather | A61B 17/1617 606/83 |
| 2013/0296864 A1 | 11/2013 | Burley et al. | |
| 2014/0324052 A1 | 10/2014 | Carrison et al. | |
| 2014/0336653 A1 | 11/2014 | Bromer | |
| 2014/0336654 A1 | 11/2014 | Pilgeram | |

* cited by examiner

*Primary Examiner* — Anu Ramana
(74) *Attorney, Agent, or Firm* — Taylor IP, P.C.

(57) ABSTRACT

An orthopedic driver includes a drivetrain having a driven end and a second end opposite the driven end, the drivetrain defining a first axis; an instrument connector rotatably coupled to the second end of the drivetrain and defining a second axis angled relative to the first axis; an angling bushing associated with the instrument connector; and a housing having a straight portion covering at least a portion of the drivetrain and an angled portion connected to the straight portion, the angled portion interacting with the angling bushing to hold the instrument connector angled relative to the drivetrain.

15 Claims, 4 Drawing Sheets

ANGLED ORTHOPAEDIC DRIVER

BACKGROUND OF THE INVENTION

1. Field of the Invention

The present invention relates to orthopaedic drivers, and, more particularly, to angled orthopaedic drivers.

2. Description of the Related Art

When performing orthopaedic procedures, orthopaedic drivers are often used to connect a driven instrument, such as a reamer head, to a power drill or other rotating element in order to rotate the instrument. Typical orthopaedic drivers include a shank that couples with the rotating element and a drive shaft to transmit rotation from the shank to a driving end that connects to the driven instrument. This arrangement allows the drill to be held outside the body while the driven instrument is used.

As orthopaedic surgical techniques have evolved, angled orthopaedic drivers have become more popular. In an angled orthopaedic driver, the drive shaft defines an axis and the connected instrument is held at an angle relative to the axis. Such a configuration can allow for the orthopaedic surgery to be performed through a smaller incision. Examples of such devices are known from, for example, U.S. Pat. No. 8,480,674 to Rogers et al. which teaches an orthopaedic driver utilizing Cardan joints including U-joints and H-joints to drive an instrument. As taught by Rogers et al., the beveled relationship between a proximal U-joint and an H-joint of the drivetrain enables articulation of the H-joint through a range of angles, which allows the angle of the connected instrument to be altered. One problem with this construction is that the beveling of the U-joint and H-joint controls the angling of the connected instrument. Since the U-joint and H-joint of the drivetrain are not components that can be easily swapped out between or during surgeries, the angling of the driven instrument relative to the drivetrain is not easily adjustable. During surgery, a surgeon may discover that the originally chosen angling of the driven instrument is not the desired angle for the procedure. Since the angling of the driven instrument relative to the drivetrain is not easily adjustable, due to the U-joint and H-joint beveling controlling the angling, a surgeon may use an undesired angling during the procedure or will have to obtain a different orthopaedic driver that has been pre-configured with a different angling.

What is needed in the art is an orthopaedic driver that is more easily adjustable than known orthopaedic drivers.

SUMMARY OF THE INVENTION

The present invention provides an orthopaedic driver that includes an instrument connector and an angling bushing associated with the instrument connector that interacts with a housing of the orthopaedic driver to angle the instrument connector.

The invention in one form is directed to an orthopaedic driver that includes: a drivetrain having a driven end and a second end opposite the driven end, the drivetrain defining a first axis; an instrument connector rotatably coupled to the second end of the drivetrain and defining a second axis angled relative to the first axis; an angling bushing associated with the instrument connector; and a housing having a straight portion covering at least a portion of the drivetrain and an angled portion connected to the straight portion, the angled portion interacting with the angling bushing to hold the instrument connector angled relative to the drivetrain.

The invention in another form is directed to a method of adjusting an angling of an orthopaedic driver that includes providing an orthopaedic driver having a drivetrain defining a first axis, an instrument connector rotatably coupled to the drivetrain and defining a second axis that is angled relative to the first axis, and a housing having a straight portion at least partially covering the drivetrain and an angled portion interacting with the instrument connector to hold the instrument connector at a first angle relative to the drivetrain. The housing is separated from the drivetrain and the instrument connector and replaced with a different housing, the different housing having a straight portion at least partially covering the drivetrain and an angled portion interacting with the instrument connector to hold the instrument connector at a second angle relative to the drivetrain.

An advantage of the present invention is the angling of the instrument connector relative to the drivetrain can be easily and quickly adjusted by swapping out the housing.

Another advantage is the angling of the instrument connector relative to the drive train can be adjusted to a wide variety of angles.

Yet another advantage is the angling bushing angles the instrument connector while providing smooth rotation of the instrument connector during operation.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
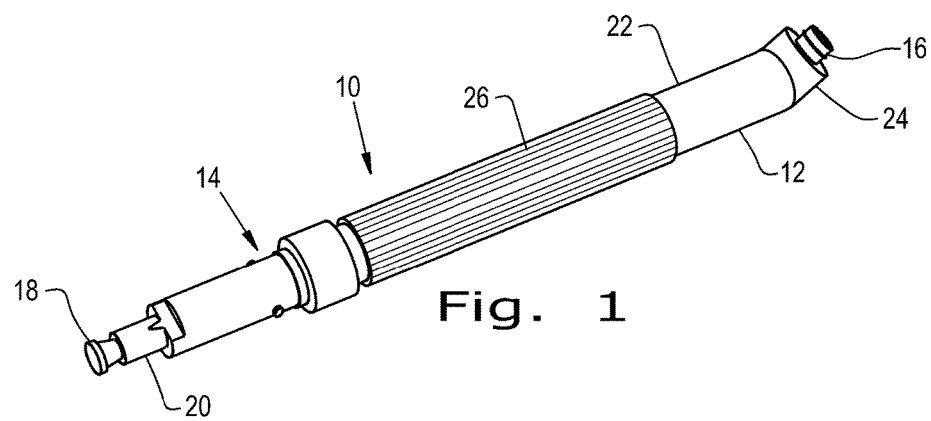
FIG. 1 is a perspective view of an embodiment of an orthopaedic driver according to the present invention.
Figure 7:
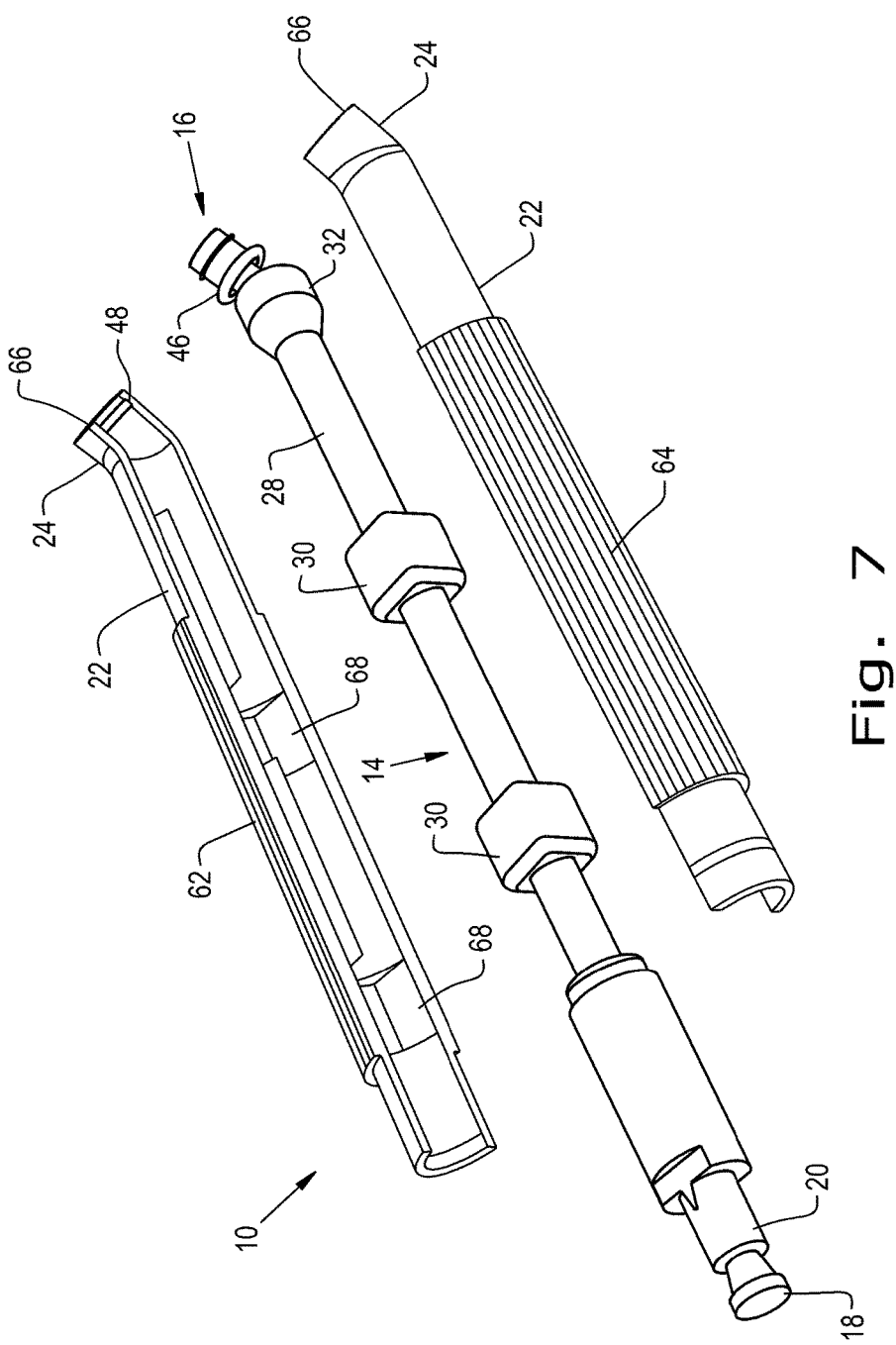
FIG. 7 is a perspective view of a housing of the orthopaedic driver being separated from the drivetrain.

Referring now to the drawings, and more particularly to FIG. 1, there is shown an embodiment of an orthopaedic driver 10 according to the present invention which generally includes a housing 12, a drivetrain 14 (shown separately from the housing 12 in FIG. 2) held within the housing 12, and an instrument connector 16 rotatably coupled to the drivetrain 14. As can be seen, the drivetrain 14 includes a driven end 18 with a shank 20 that can connect to a source of rotational motion, such as a power drill, to rotate the drivetrain 14 and transmit the rotational motion to the instrument connector 16 via the rotational coupling to the drivetrain 14. The housing 12 has a straight portion 22 that can cover most of the rotating parts of the drivetrain 14 and an angled portion 24 that can partially cover the instrument connector 16, which will be described further herein. The housing 12 can have additional features such as a texture 26 formed on the outer surface of the housing 12 to improve a user's grip during surgery. Further, the housing 12 can be separable (as shown in FIG. 7) to allow for easy disassembly and processing, as well as altering the angle of the instrument connector 16, which will be described further herein.

Figure 2:
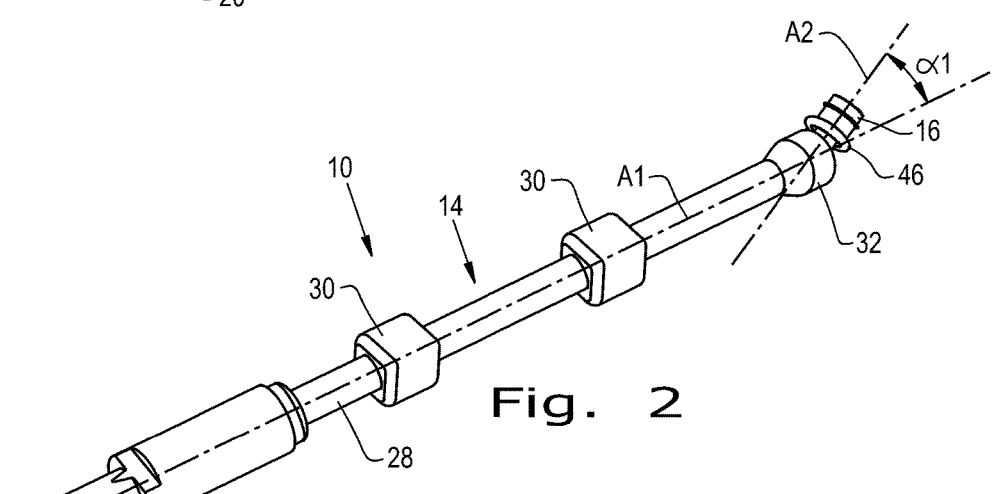
FIG. 2 is a perspective view of the orthopaedic driver shown in FIG. 1 with the housing removed.

Referring now to FIG. 2, the orthopaedic driver 10 is shown without the housing 12 to better illustrate and explain the other components of the driver 10. As can be seen, the drivetrain 14 includes a drive shaft 28 connected to the shank 20 that will be rotated by the shank 20 as the shank 20 is rotated by a connected rotating element. The drive shaft 28 defines a first axis A1, which will be the axis of rotation that the drive shaft 28 rotates about. It should be appreciated that the drive shaft 28 and first axis A1 can be described interchangeably since the drive shaft 28 defines the first axis A1. To keep the drive shaft 28 stable within the housing 12, one or more drive bushings 30 can be fit to the drive shaft 28 and contact an interior of the housing 12. The drive bushings 30 will therefore help keep the drive shaft 28 statically situated within the housing 12 to prevent the drive shaft 28 from coming in contact with the housing 12 and damaging either the drive shaft 28 or the housing 12. The drive bushings 30 can be formed of a low friction material, such as polyethylene, so that there is little loss of mechanical force and buildup of heat between the drive bushings 30 and the drive shaft 28 due to friction. The drive bushings 30 can be cubic shaped, as shown, that will not rotate relative to the housing 12 or different shapes, depending on the configuration of the housing 12.

The drivetrain 14 has a second end 32 opposite the driven end 18 that rotatably couples to the instrument connector 16. As can be seen, the instrument connector 16 defines a second axis A2 that is angled relative to the first axis A1 defined by the drive shaft 28, so that the instrument connector 16 and a connected instrument (not shown) are angled relative to the first axis A1. The second axis A2 is angled relative to the first axis A1 to define a first angle α1, which can be the angle that the connected instrument forms relative to the drive shaft 28. The second end 32 can be a flared end that has a first radius that is approximately equal to the radius of the drive shaft 28 that widens toward a second radius which is greater than the first radius and allows the coupled instrument connector 16 to swivel within the housing 12. The second radius of the flared end 32 can therefore be the limit to how much the instrument connector 16 is allowed to swivel within the housing 12. While the drivetrain 14 is shown with a flared end 32, a flared collar or similar construction could also be incorporated adjacent the second end 32 of the drivetrain 14 to limit the amount of swiveling that the instrument connector 16 is allowed within the housing 12.

Figure 3:
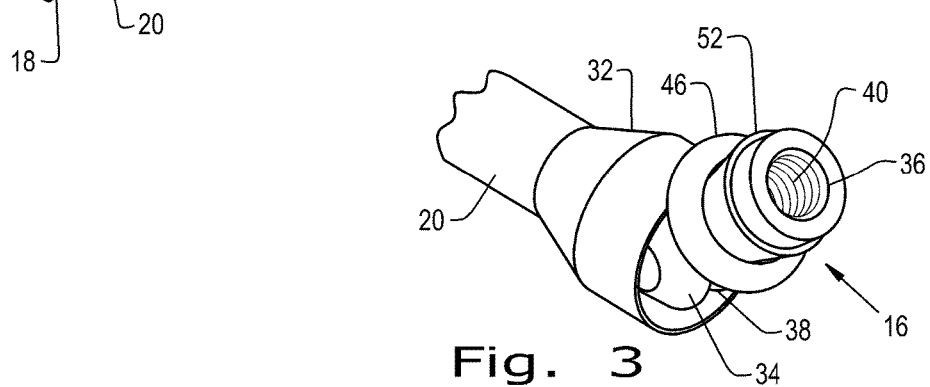
FIG. 3 is a close-up perspective view of the orthopaedic driver shown in FIG. 2.
Figure 4:
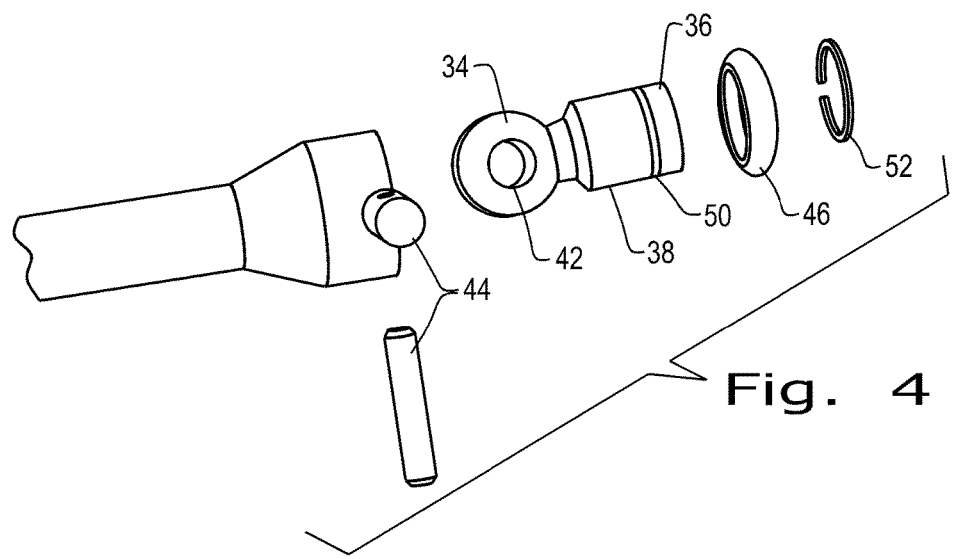
FIG. 4 is an exploded view of an end of the orthopaedic driver shown in FIGS. 2-3.

Referring now to FIGS. 3 and 4, the rotatable coupling between the drivetrain 14 and the instrument connector 16 is shown in better detail. The instrument connector 16 can include a rotational coupling 34 that is rotatably coupled to the drivetrain 14, an instrument coupling 36 that is configured to connect to an instrument, and a base 38 connecting the rotational coupling 34 and instrument coupling 36. As can be seen in FIG. 3, the instrument coupling 36 can be a threaded opening formed in the instrument connector 16 that has threads 40 formed therein that will interact with threads of an instrument to connect the instrument to the instrument connector 16 and allow rotational energy from the drivetrain 14 to be transmitted to the instrument. The rotational coupling 34, as shown, can have a spherical shape and pin openings 42 formed therein that will connect to the drivetrain 14, such as the flared end 32 of the drivetrain 14, so that rotational motion of the drive shaft 28 will cause rotational motion of the rotational coupling 34, and therefore the entire instrument connector 16. The rotational coupling 34 can be rotatably coupled to the flared end 32 by pins 44 held within the pin openings 42 of the rotational coupling 34 and connected to the flared end 32. It should be appreciated that the instrument coupling 36 and rotational coupling 34 shown and described herein are exemplary only and any type of such couplings can be incorporated in the instrument connector according to the present invention.

The orthopaedic driver 10 further includes an angling bushing 46 that is associated with the instrument connector 16 and interacts with the angled portion 24 of the housing 12 to hold the instrument connector 16 at the first angle α1 relative to the drive shaft 28. As used herein, "associated with" is intended to mean that the angling bushing 46 has some sort of relationship with the instrument connector 16, such as the angling bushing 46 being fit over or onto the base 38 of the instrument connector 16, that causes the relative orientation of the angling bushing 46 to the first axis A1 to define the relative orientation of the instrument connector 16 to the first axis A1. As shown in FIG. 3, the angling bushing 46 is fit onto the base 38 of the instrument connector 16 to surround part of the base 38 and held in a bushing groove 48 (shown in FIG. 7) of the angled portion 24 of the housing 12 so that the instrument connector 16 is held at the first angle α1 relative to the drive shaft 28. In this sense, the orientation of the angling bushing 46 relative to the drive shaft 28 controls the angle formed between the first axis A1 defined by the drive shaft 28 and the second axis A2 defined by the instrument connector 16. This allows the angle formed between the drive shaft 28 and the instrument connector 16 to be changed through adjustment of the relative orientation of the angling bushing 46 to the drive shaft 28 by altering how the angled portion 24 of the housing 12 interacts with the angling bushing 46, which will be described further herein. Since the housing 12 can be separable and it may be useful for the angling bushing 46 to be able to slide along the base 38 of the instrument connector 16, the instrument connector 16 can have a retaining groove 50 formed therein that a retaining ring 52 is held within. The retaining ring 52 can have a thickness that, when held in the retaining groove 50, prevents the angling bushing 46 from sliding off the base 38 of the instrument connector 16 if the housing 12 is separated from the drivetrain 14 and no longer interacting with the angling bushing 46. As shown, the angling bushing 46 is a ring bushing that can comprise a low friction polymer material, such as polyethylene, but the angling bushing 46 can be formed in any suitable shape and of any suitable material to interact with the angled portion 24 of the housing 12 to hold the instrument connector 16 angled relative to the drive shaft 28.

Figure 5:
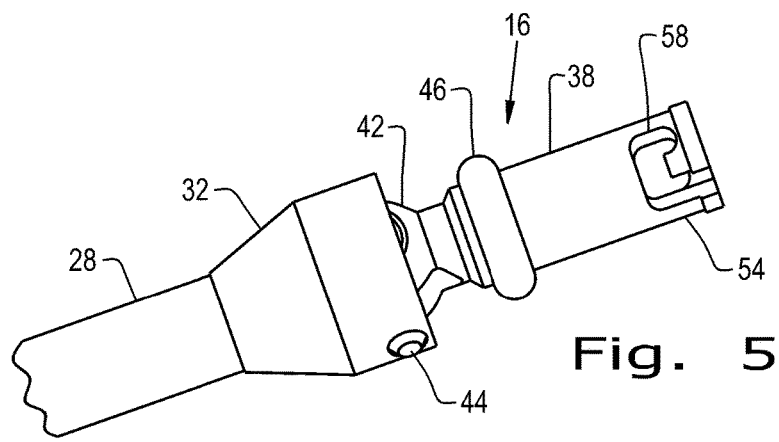
FIG. 5 is a perspective view of the orthopaedic driver shown in FIGS. 1-4 with a different instrument connector.
Figure 6:
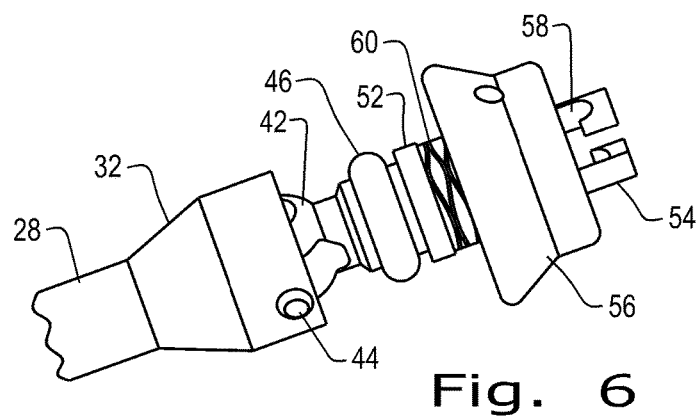
FIG. 6 is another perspective view of the orthopaedic driver shown in FIGS. 1-4 with another different instrument connector.

Referring now to FIGS. 5 and 6, it can be seen that the threaded opening 36 of the instrument connector 16 shown in FIG. 3 can be replaced with a different instrument coupling to connect to different types of instrument. As shown in FIG. 5, the instrument coupling can be a bayonet connection 54 that will interact with a bayonet connector on an instrument to connect the instrument to the instrument connector 16. Another option is to couple the bayonet connection 54 shown in FIG. 5 with a pull-back collar 56, as shown in FIG. 6, that is spring actuated and can lock pins of an instrument in a slot 58 of the bayonet connection 54. The pull-back collar 56 can be actuated by a spring 60 that is held between the pull-back collar 56 and the retaining ring 52, as shown in FIG. 6.

Referring now to FIG. 7, the orthopaedic driver 10 is shown with the housing 12 being separated from the drivetrain 14. The housing 12 can therefore include a first piece 62 that is separable from a second piece 64 to separate from the drivetrain 14. The first piece 62 and second piece 64 can be separable from one another in any desired way. As can be seen, the bushing groove 48 where the angling bushing 46 can be held can be formed adjacent to an end 66 of the angled portion 24 of the housing 12 so that the angled portion 24 does not cover an entirety of the instrument connector 16, just the rotational coupling 34 and a portion of the base 38, when the instrument connector 16 is angled by the interaction between the angling bushing 46 and the angled portion 24. Further, the straight portion 22 can have bearing grooves 68 formed therein that the drive bushings 30 can be held within. The bearing grooves 68 can have a shape that does not allow the drive bushings 30 to rotate relative to the housing 12, as previously described.

Figure 8:
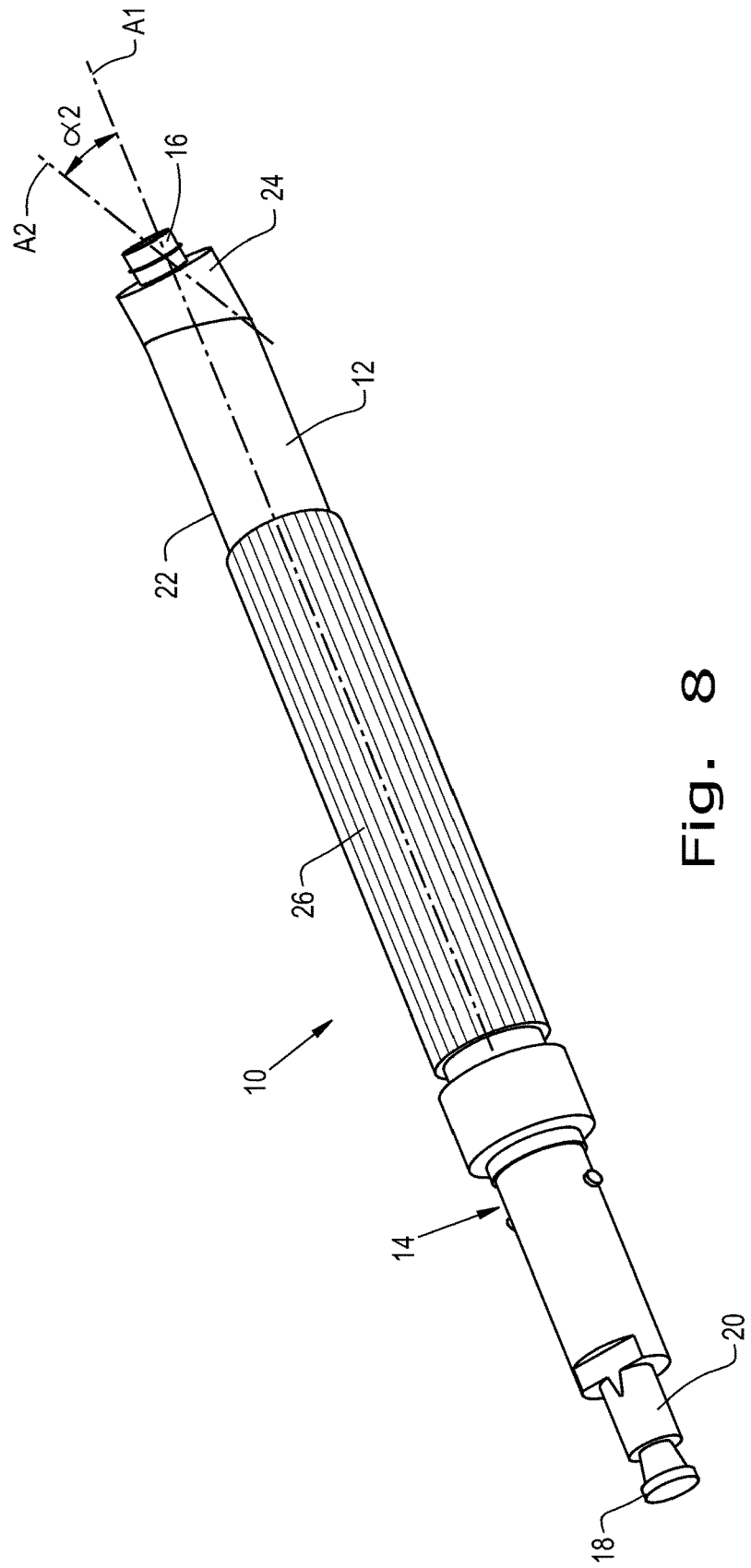
FIG. 8 is a perspective view of the orthopaedic driver shown in FIG. 7 with a different housing that replaces the housing shown being separated from the orthopaedic driver in FIG. 7.

As can be surmised, when the angling bushing 46 is held in the bushing groove 48 of the angled portion 24 of the housing 12, the angling bushing 46 is held at the first angle α1 relative to the drive shaft 28. Since the angling bushing 46 is associated with the instrument connector 16, the instrument connector 16 is also held at the first angle α1 by its association with the angling bushing 46. In other words, the first angle α1 that the instrument connector 16 is held at approximates the relative angle formed between the straight portion 22 and the angled portion 24 of the housing 12. During a procedure, it may be found that the instrument connector 16 and connected instrument (not shown) being held at the first angle α1 relative to the drive shaft 28 is not the optimum angle for the procedure. In such an event, the user can separate the housing 12 from the drivetrain 14, as shown in FIG. 7, and replace the housing 12 with a different housing 70, as shown in FIG. 8, which also has a straight portion 72 that will cover part of the drivetrain 14 and an angled portion 74 connected to the straight portion 72 that will interact with the angling bushing 46 to hold the instrument connector 16 at a second angle α2 relative to the drive shaft 28. As can be seen, the relative angle formed between the straight portion 72 and the angled portion 74 of the housing 70 is different than the angle formed between the straight portion 22 and the angled portion 24 of the housing 12, so the second angle α2 that the instrument connector 16 is held at when the angled portion 74 of the housing 70 interacts with the angling bushing 46 is different than the first angle α1 that the instrument connector 16 was previously held at when the angled portion 24 of the housing 12 interacted with the angling bushing 46. The second angle α2 can be less than the first angle α1, as shown. It can therefore be seen that the angle that the instrument connector 16 is held at relative to the drive shaft 28 can be quickly and easily adjusted by removing the housing of the orthopaedic driver 10 and replacing the housing with another housing that has a different angle formed between a straight portion and an angled portion of the housing.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic driver, comprising:
   a drivetrain having a driven end and a second end opposite said driven end, said drivetrain defining a first axis;
   an instrument connector rotatably coupled to said second end of said drivetrain and defining a second axis angled relative to said first axis;
   an angling bushing associated with said instrument connector; and
   a housing having a straight portion covering at least a portion of said drivetrain and an angled portion connected to said straight portion, said housing including a bushing groove formed adjacent to an end of said angled portion, said angling bushing being held in said bushing groove within said housing, and said angled portion interacting with said angling bushing to hold said instrument connector angled relative to said drivetrain.

2. The orthopaedic driver according to claim 1, wherein said instrument connector includes a rotational coupling coupled to said drive train, an instrument coupling configured to connect to an instrument, and a base connecting said rotational coupling to said instrument coupling, said angling bushing at least partially surrounding said base.

3. The orthopaedic driver according to claim 2, wherein said rotational coupling defines one end of said instrument connector and said instrument coupling defines another end of said instrument connector opposite said rotational coupling.

4. The orthopaedic driver according to claim 3, further comprising a retaining ring affixed to said base between said angling bushing and said instrument coupling, said retaining ring preventing said angling bushing from sliding off said base.

5. The orthopaedic driver according to claim 3, wherein said angled portion of said housing surrounds said rotational coupling.

6. The orthopaedic driver according to claim 1, wherein said instrument connector includes at least one of a threaded opening, a bayonet connector, and a pull-back collar.

7. The orthopaedic driver according to claim 1, wherein said angling bushing has a shape of a ring.

8. The orthopaedic driver according to claim 7, wherein said angling bushing comprises a polymer.

9. The orthopaedic driver according to claim 1, further comprising at least one additional bushing placed over said drivetrain and contacting an interior of said straight portion of said housing.

10. The orthopaedic driver according to claim 9, wherein said at least one additional bushing is held within a bearing groove formed in said interior of said straight portion.

11. The orthopaedic driver according to claim 9, wherein said at least one additional bushing has a cubic shape.

12. The orthopaedic driver according to claim 1, wherein said second end of said drivetrain is a flared end.

13. The orthopaedic driver according to claim 1, wherein said housing a separable housing.

14. A method of adjusting an angling of an orthopaedic driver, comprising the steps of:

providing an orthopaedic driver having a drivetrain defining a first axis and having a driven end and a second end opposite said driven end, an instrument connector rotatably coupled to said second end of the drivetrain and defining a second axis that is angled relative to said first axis, an angling bushing associated with said instrument connector, and a housing having a straight portion at least partially covering said drivetrain and an angled portion connected to said straight portion, said housing including a bushing groove formed adjacent to an end of said angled portion so that said angling bushing is held in said bushing groove within said housing, and said angling bushing interacting with said angled portion of said housing to hold said instrument connector at a first angle relative to said drivetrain;

separating said housing from said drivetrain and said instrument connector; and replacing said housing with a different housing, said different housing having a straight portion at least partially covering said drivetrain and an angled portion, said angling bushing interacting with said angled portion of said different housing to hold said instrument connector at a second angle relative to said drivetrain.

15. The method according to claim 14, wherein said second angle is one of greater than and less than said first angle.

* * * * *